(12) United States Patent
Keri et al.

(10) Patent No.: US 7,425,644 B2
(45) Date of Patent: Sep. 16, 2008

(54) METHOD OF PURIFYING PRAVASTATIN

(75) Inventors: Vilmos Keri, Debrecen (HU); Istvan Melczer, Debrecen (HU)

(73) Assignee: TEVA Gyógyszergyár Zártkörűen Működő Részvénytársaság, Debrecen (HU)

( * ) Notice: Subject to any disclaimer, the term of this patent is extended or adjusted under 35 U.S.C. 154(b) by 481 days.

(21) Appl. No.: 10/996,238

(22) Filed: Nov. 23, 2004

(65) Prior Publication Data

US 2005/0113446 A1    May 26, 2005

Related U.S. Application Data

(60) Provisional application No. 60/554,165, filed on Mar. 18, 2004, provisional application No. 60/532,314, filed on Dec. 22, 2003, provisional application No. 60/525,494, filed on Nov. 24, 2003.

(51) Int. Cl.
| C07C 69/74 | (2006.01) |
| C07C 69/66 | (2006.01) |
| C07C 65/00 | (2006.01) |

(52) U.S. Cl. .................. 560/119; 560/188; 562/466
(58) Field of Classification Search .................. 560/119, 560/188; 562/466
See application file for complete search history.

(56) References Cited

U.S. PATENT DOCUMENTS

| 4,319,039 | A | 3/1982 | Albers-Schonberg |
| 4,346,227 | A | 8/1982 | Terahara et al. |
| 4,410,629 | A | 10/1983 | Terahara et al. |
| 4,857,522 | A | 8/1989 | DiPietro et al. |
| 4,857,547 | A | 8/1989 | Hoffman et al. |
| 5,099,035 | A | 3/1992 | Saunders et al. |
| 5,140,012 | A | 8/1992 | McGovern et al. |
| 5,153,124 | A | 10/1992 | Furuya et al. |
| 5,157,025 | A | 10/1992 | Aberg et al. |
| 5,180,589 | A | 1/1993 | Joshi et al. |
| 5,202,029 | A | 4/1993 | Haytko et al. |
| 5,616,595 | A | 4/1997 | Chu et al. |
| 5,712,130 | A | 1/1998 | Hajko et al. |
| 5,883,109 | A | 3/1999 | Gregg et al. |
| 5,942,423 | A | 8/1999 | Demain et al. |
| 6,444,452 | B1 | 9/2002 | Keri et al. |
| 6,682,913 | B1 | 1/2004 | Jekkel et al. |
| 6,695,969 | B1 | 2/2004 | Grahek et al. |
| 6,696,599 | B2 | 2/2004 | Jekkel et al. |
| 6,750,366 | B2 | 6/2004 | Jekkel et al. |
| 2004/0039225 | A1 | 2/2004 | Jekkel et al. |

FOREIGN PATENT DOCUMENTS

| EP | 0 215 665 | 3/1987 |
| EP | 0 605 230 | 7/1994 |
| EP | 0 642 530 | 3/1995 |
| EP | 0 671 170 | 9/1995 |
| JP | 11-235174 | 8/1999 |
| WO | WO 92/16276 | 10/1992 |
| WO | WO 97/06128 | 2/1997 |
| WO | WO 98/37220 | 8/1998 |
| WO | WO 98/45410 | 10/1998 |
| WO | WO 99/10499 | 3/1999 |
| WO | WO 99/42601 | 8/1999 |
| WO | WO 00/17182 | 3/2000 |
| WO | WO 00/46175 | 8/2000 |
| WO | WO 01/03647 | 1/2001 |
| WO | WO 01/10813 | 2/2001 |
| WO | WO 01/81611 | 11/2001 |
| WO | WO 02/30415 | 4/2002 |

OTHER PUBLICATIONS

Budavari, et al. The Merck Index. 1989. Merck and Co., Inc., p. 1222.
T. Koga et al., "Tissue-selective inhibition of cholesterol synthesis in vivo by pravastatin sodium, a 3-hydroxy-3-methyglutaryl coenzyme A reductase inhibitor", Biochimica et Biophysica Acta, vol. 1045, No. 1, pp. 115-120, Jun. 28, 1990.
Serajuddin et al. "Relative Lipophilicities, Solubilities, and Structure-Pharmacological Considerations of 3-Hydroxy-3-Methylglutaryl-Coenzyme A (HMG-CoA) Reductase Inhibitors Pravastatin, Lovastatin, Mevastatin, and Simvastatin", Journal of Pharmaceutical Sciences, vol. 80, No. 9, pp. 830-834, Sep. 1991.
McMaster, Chem 2O6 Lab Manual, 1997, http://www.chemistry.mcmaster.ca/~chem2o6/labmanual/expt1/exp1b-i.html, pp. 1-9.
Pantoja et al., "Steroids Isolated from Lophogorgia Platycados", J. Nat. Prod., vol. 49, No. 2, p. 357-358, 1986.

*Primary Examiner*—Taylor Victor Oh
(74) *Attorney, Agent, or Firm*—Kenyon & Kenyon LLP

(57) ABSTRACT

The present invention provides pure pravastatin compositions and pure compactin compositions, and methods for the preparation thereof.

42 Claims, No Drawings

METHOD OF PURIFYING PRAVASTATIN

CROSS-REFERENCE TO RELATED APPLICATIONS

This application claims the benefits of U.S. Provisional Patent Application Nos. 60/525,494, filed Nov. 24, 2003, 60/532,314, filed Dec. 22, 2003, and 60/554,165, filed Mar. 18, 2004, the contents of all of which are incorporated herein by reference.

FIELD OF THE INVENTION

The invention encompasses methods for isolating and purifying pravastatin from reactions conducted in aqueous fermentation broths. In particular, the invention encompasses the synthesis, isolation, and purification of pravastatin, such as pravastatin made by the fermentation of compactin.

BACKGROUND OF THE INVENTION

Complications of cardiovascular disease, such as myocardial infarction, stroke, and peripheral vascular disease account for half of the deaths in the United States. A high level of low density lipoprotein (LDL) in the bloodstream has been linked to the formation of coronary lesions which obstruct the flow of blood and can rupture and promote thrombosis. Goodman and Gilman, THE PHARMACOLOGICAL BASIS OF THERAPEUTICS, p. 879 (9th ed., 1996). Reducing plasma LDL levels has been shown to reduce the risk of clinical events in patients with cardiovascular disease and in patients who are free of cardiovascular disease but who have hypercholesterolemia. Scandinavian Simvastatin Survival Study Group, 1994; Lipid Research Clinics Program, 1984a, 1984b.

Statin drugs are currently the most therapeutically effective drugs available for reducing the level of LDL in the blood stream of a patient at risk for cardiovascular disease. This class of drugs includes, inter alia, compactin, lovastatin, simvastatin, pravastatin and fluvastatin. The mechanism of action of statin drugs has been elucidated in some detail. The statin drugs disrupt the synthesis of cholesterol and other sterols in the liver by competitively inhibiting the 3-hydroxy-3-methyl-glutaryl-coenzyme A reductase enzyme ("HMG-CoA reductase"). HMG-CoA reductase catalyzes the conversion of HMG-CoA to mevalonate, which is the rate determining step in the biosynthesis of cholesterol. Consequently, HMG-CoA reductase inhibition leads to a reduction in the rate of formation of cholesterol in the liver.

Pravastatin is the common medicinal name of the chemical compound [1S-[1α(β*, δ*)2α,6α,8β(R*),8aα]]-1,2,6,7,8,8a-hexahydro-β,δ,6-trihydroxy-2-methy-8-(2-methyl-1-oxobutoxy)-1-naphthalene-heptanoic acid. (CAS Registry No. 81093-370.) The molecular structure of pravastatin in free acid form is represented by Formula (I):

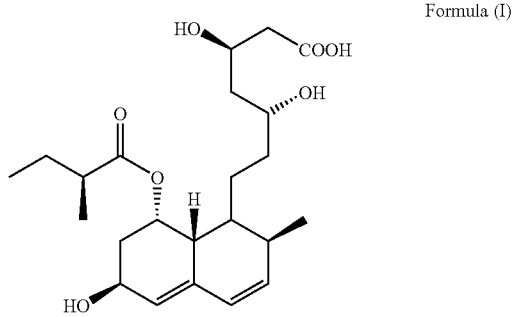

Formula (I)

Pravastatin possesses an alkyl chain that is terminated by a carboxylic acid group closed in a lactone and that bears two hydroxyl groups, one at the β position and a second at the δ position, with respect to the carboxylic acid group. The alkyl chain is the portion of the molecule that binds to HMG-CoA reductase. The carboxylic acid group and the hydroxyl group at the δ position are prone to lactonize. Compounds that form a lactone, like the statins, may exist either in the free acid form or the lactone form or in an equilibrium mixture of both forms. Compounds that form lactones cause processing difficulties during the manufacture of statin drugs because the free acid and the lactone form of the compounds have different polarities. One method of purifying one form will remove impurities but also is likely to remove the other form thereby resulting in a lower overall yield. Consequently, great care must be exercised when handling lactonizable compounds to isolate them in high yield.

Pravastatin exhibits an important therapeutic advantage over other statins. Pravastatin selectively inhibits cholesterol synthesis in the liver and small intestine but leaves cholesterol synthesis in the peripheral cells substantially unaffected. Koga, T. et al., Biochim. Biophys. Acta, 1045, 115-120 (1990). The selectivity appears to be due, in part, to the presence of a hydroxyl group at the C-6 position of the hexahydronaphthalene nucleus. The C-6 position is occupied by a hydrogen atom in compactin and a methyl group in lovastatin. Pravastatin is less able to permeate the lipophilic membranes of peripheral cells than the other more lipophilic congeners. Serajuddin et al., J. Pharm. Sci., 80, 830-34 (1991). Also, the limited mobility of pravastatin is thought to account for its more localized action in the liver and intestine.

According to the U.S. Pat. No. 4,346,227 patent, pravastatin can be obtained by fermentation of compactin using a variety of microorganisms: Absidia coerulea IFO 4423 spores, Cunninghamella echinulata IFO 4445, Streptomyces rosochromogenus NRRL 1233, Syncephalastrum racemosum IFO 4814 and Syncephalastrum racemosum IFO 4828. In example 1 of the '227 patent, after fermentation pravastatin was separated from the fermentation broth by acidifying the broth to a pH of 3 and extracting pravastatin and other non-hydrophilic organics with ethyl acetate, followed by washing with brine. The pravastatin free acid was lactonized by addition of a catalytic amount of trifluoroacetic acid, then neutralized with dilute sodium bicarbonate, dried over sodium sulfate and evaporated to dryness. The residue was purified by preparative reverse-phase high performance liquid chromatography ("HPLC").

U.S. Pat. No. 5,942,423 discloses the microbial hydroxylation of compactin to pravastatin using a strain of Actinomadura. In the preferred embodiments, the pravastatin is isolated, enriched, separated, or purified, using commonly known techniques such as precipitation, extraction, and chromatography. HPLC is disclosed as the preferred method of isolation of pravastatin from the fermentation broth.

U.S. Pat. No. 5,202,029 discusses a process for the purification of HMG-CoA reductase inhibitors using HPLC. One skilled in the art will recognize that HPLC is not an economical purification method for large-scale preparation of chemical compounds and difficulties associated with high volume purification may discourage the use of HPLC. After impurity separation on the HPLC column, the HMG-CoA reductase inhibitor is eluted from the HPLC column as a solute dissolved in the eluent. The eluent is partially evaporated and then water is added to induce crystallization of the HMG-CoA reductase inhibitor.

U.S. Pat. No. 5,616,595 discloses a continuous process for recovering water-insoluble compounds from a fermentation broth by tangential filtration. The fermentation broth is cycled past a filter and becomes increasingly concentrated with each cycle because of water loss through the filter. Once a desired concentration is reached, the concentrated broth is slurried with a solvent in which the desired compound is soluble. The slurry is then cycled past the filter. The desired compound is collected as a filtrate and subsequently isolated from the filtrate. Optionally, the compound may be further purified. The patent states that the method is applicable to a wide variety of compounds including lovastatin, pravastatin and simvastatin.

Presently, the most economically feasible method of making pravastatin is by enzymatic hydroxylation of compactin at the C-6 position. The known methods for isolating a statin from a fermentation broth, however, are ill-suited for isolating pure pravastatin, in particular from the pravastatin sodium salt. Moreover, the currently employed methods do not achieve pharmaceutically acceptable levels of purity, or alternatively, require economically impractical chromatographic separation to achieve high purity.

SUMMARY OF THE INVENTION

The invention encompasses methods of synthesizing pravastatin comprising less than about 0.1% by weight pravastatin C comprising:
 a) purifying compactin containing compactin C until the amount of compactin C is less than about 0.16% by weight, and
 b) synthesizing pravastatin using the compactin from a).
   The purifying step in a) may be performed by a crystallization process comprising dissolving or suspending compactin in at least one water miscible organic solvent; adding water in a volume ratio of about 0.16 to about 0.4 to the water miscible organic solvent to the reaction mixture; cooling the reaction mixture to a temperature in which compactin crystallizes; and collecting the pure compactin crystals.

In another embodiment, the invention encompasses compactin prepared according to the crystallization process described above, and pharmaceutical formulations comprising thereof.

In one embodiment, the invention encompasses methods of synthesizing pravastatin having less than about 0.1% by weight pravastatin C comprising:
 a) dissolving or suspending a composition comprising compactin and compactin C in at least one water miscible organic solvent;
 b) adding water in a volume ratio of about 0.16 to about 0.4 to the water miscible organic solvent;
 c) cooling the reaction mixture;
 d) isolating a sample of the composition comprising compactin and compactin C resulting from c);
 e) measuring the quantity of compactin C in the isolated sample from d);
 f) determining whether or not the quantity of compactin C in e) is less than about 0.16% by weight; and
 g) purifying by crystallization the composition resulting from d) if the quantity of compactin C measured in e) is about 0.16% by weight or more until the quantity of compactin C is less than about 0.16% by weight, and synthesizing a pravastatin composition from the composition so purified; or,
 h) if the quantity of compactin C measured in e) is less than about 0.16% by weight, synthesizing a pravastatin composition from the composition of step d).

In another embodiment, the invention encompasses pravastatin comprising less than about 0.1% pravastatin C by weight made by a fermentation of compactin having less than 0.16% compactin C by weight, and pharmaceutical formulations comprising thereof.

In yet another embodiment, the invention encompasses methods of synthesizing pravastatin by hydroxylation of compactin, wherein the compactin contains less than about 0.16% by weight of compactin C.

In one embodiment, the invention provides a method for preparing a composition comprising pravastatin sodium having less than about 0.1% by weight pravastatin C. The method includes starting with a compactin sample comprising a sufficiently low level of compactin C. Preferably, the amount of compactin C in the compactin sample is less than about 0.16% by weight. The method comprises:
 a) obtaining at least one sample of at least one compactin batch;
 b) measuring the level of compactin C in the sample of a);
 c) selecting the compactin batch comprising less than about 0.16% compactin C by weight, based on the measurement or measurements conducted in b); and
 d) using the batch selected in c) to synthesize pravastatin sodium.

In another embodiment, the invention provides a composition comprising pravastatin sodium having less than about 0.1% by weight pravastatin C, and pharmaceutical formulations comprising thereof.

In yet another embodiment, the invention provides compactin compositions comprising less than about 0.16% by weight compactin C and pharmaceutical formulations comprising thereof.

In one embodiment, the invention provides a process for purifying pravastatin which comprises dissolving pravastatin salt in water to form an aqueous solution of pravastatin; adjusting the pH of the aqueous solution of pravastatin to a pH of about 6.7 to about 10; contacting the pravastatin aqueous solution to an adsorption column bed; eluting pravastatin with an eluting solution; and collecting fractions having pure pravastatin. The pravastatin salt in the aqueous solution may be obtained by hydroxylation of compactin.

In another embodiment, the present invention provides pravastatin produced by this purification process, and pharmaceutical formulations comprising thereof.

DETAILED DESCRIPTION OF THE INVENTION

The methods of the present invention produce high purity pravastatin by: i) using relatively pure starting materials to synthesize pravastatin or ii) using adsorption chromatography. Therefore in one aspect of the present invention, high purity pravastatin is synthesized by using pure compactin, which is obtained by at least one step of purifying the compactin prior to pravastatin synthesis, or by selecting a batch of pure compactin.

The high purity and high yield pravastatin is obtained without the need for multiple extractions, or purification by HPLC. Therefore the invention is more cost effective and practical than previous methods for isolating pravastatin, meeting the need in the art for an economically practical method of preparing pravastatin on a preparative scale.

As used herein, the term "pravastatin C" (used also in the European Pharmacopoeia) refers to the pravastatin impurity having the chemical name 3S,5S-3,5-dihydroxy-7-[(1S,2S, 6S,8S,8aR)-6-hydroxy-2-methyl-8-[[(2S)-2-methylpentanoyl]oxy]-1,2,6,7,8,8a-hexahydronaphtalen-1-yl]heptanoic acid.

As used herein, the term "compactin C" refers to the compactin impurity having the chemical name pentanoic acid, 2-methyl-, 1,2,3,7,8,8a-hexahydro-7-methyl-8-[2-(tetrahydro-4-hydroxy-6-oxo-2H-pyran-2-yl)ethyl]-1-naphthalenyl ester, [1S-[1α(R*),7β,8β(2S*,4S*),8aβ]]. The register number is 159225-32-8.

As used herein, the term "compactin batch" refers to a composition consisting essentially of compactin, which composition may contain low levels of impurities, one of which may be compactin C. As used herein relative to a compactin batch, the term "sample" refers to a portion of the "compactin batch" that is taken for the purpose of measuring the compactin C level.

The present invention provides a method for synthesizing a pravastatin composition comprising less than about 0.1% by weight pravastatin C comprising:
a) purifying a composition comprising compactin and compactin C until a composition comprising less than about 0.16% compactin C by weight is obtained, and
b) using the composition resulting from a) to synthesize a pravastatin composition.

The composition in a) may be purified by crystallization. Preferably, the composition in a) is crystallized until it contains less than about 0.15% by weight compactin C. Preferably, the pravastatin composition synthesized in b) contains less than about 0.04% by weight pravastatin C, more preferably, less than about 0.03% by weight pravastatin C, and most preferably, the composition comprises less than about 0.02% by weight pravastatin C.

The crystallization process comprises dissolving or suspending compactin in at least one water miscible organic solvent to form a reaction mixture; adding water to the reaction mixture, in a volume of about 0.16 to about 0.4 to the water miscible organic solvent; cooling the reaction mixture to a temperature until compactin crystallizes; and collecting the pure compactin crystals. Optionally, the crystallization process may be repeated as necessary to obtain the desired compactin purity.

Preferably, the water miscible organic solvents comprise at least one of $C_{3-5}$ ketones, nitriles, and $C_{1-4}$ alcohols. More preferably, the water miscible organic solvent is at least one of acetone, methanol, ethanol, n-propanol, isopropanol, acetonitrile, methy-ethyl-ketone, or tetrahydrofuran. Most preferably, the water miscible organic solvent is at least one of acetone, methanol, ethanol, isopropanol, or acetonitrile.

The volume of water miscible organic solvent necessary to dissolve or suspend the compactin can be easily determined by one of ordinary skill in the art with little or no experimentation. The volume will vary depending upon the amount of compactin and the boiling point of the water miscible organic solvent. Typically, the volume of water miscible organic solvent is sufficient to dissolve or suspend the compactin at the reflux temperature of the water miscible organic solvent. Preferably, the volume of water miscible organic solvent is about seven times the mass of compactin, and more preferably about fives times the mass of compactin.

Preferably, the amount of water added water added is about 0.17 to about 0.4 times the volume of the water miscible organic solvent. Prior to the addition of water, the reaction mixture is heated to a temperature of about 30° C. to about reflux, and preferably to a temperature of about 20° C. to about 25° C.

The reaction mixture should be cooled to a temperature at which compactin crystallizes. The appropriate temperature may easily be determined by the skilled artisan as the temperature at which crystals become visible. Typically, the reaction mixture of compactin is cooled to a temperature from about 0° C. to about 30° C., and preferably to a temperature of about 20° C. to about 25° C. The reaction mixture is typically cooled at a rate of about 1° C. to about 6° C. per hour and preferably, at a rate of about 2° C. to about 4° C. per hour. After cooling, the reaction mixture may optionally may be heated to about 30° C. for 16 hours prior to cooling for a second time.

The compactin crystals are then collected using any method commonly known to one of ordinary skill in the art. Such methods include, but are not limited to, centrifuge, filtration funnel, belt filtration, or press filtration. Subsequently, the compactin crystals are washed with a solution of water and water miscible organic solvent, preferably in a 1:1 volume ratio. Thereafter, the collected compactin crystals are dried using techniques commonly known to one of ordinary skill in the art. The pure compactin is then used to synthesize a high purity pravastatin composition.

The present invention also provides compactin containing less than about 0.16% compactin C, and pharmaceutical formulations thereof. Preferably, compactin C is present in an amount of less than about 0.15% by weight.

The present invention further provides compactin prepared according to the above process, and pharmaceutical formulations thereof.

Another method for obtaining a pravastatin composition comprising less than about 0.1% pravastatin C comprises measuring the compactin C in samples of manufactured compactin batches. The method comprises selecting those compactin batches containing less than about 0.16% by weight compactin C, and synthesizing the pravastatin composition from the selected batches. If the compactin batch contains about 0.16% by weight compactin C or more, the compactin batch may be purified by crystallization, according to a method such as described above. One of the advantages of the present invention is that the high purity pravastatin is obtained without the need for purification by HPLC.

Measurement of compactin C in the samples of compactin batches can be conducted by standard analytical chemistry techniques, for example reverse phase HPLC or other suitable chromatographic methods. The synthesis of pravastatin sodium by enzymatic hydroxylation of compactin as well as the isolation of the pure pravastatin are described in U.S. Pat. Nos. 5,942,423 and 4,346,227, hereby incorporated by reference. The fermentation or hydroxylation broth from which pravastatin is then isolated can be any of the aqueous broths known for industrial scale fermentation of compactin.

The present invention provides a composition comprising pravastatin sodium and less than about 0.1% by weight pravastatin C, preferably, less than about 0.04% by weight pravastatin C, more preferably less than 0.03% by weight pravastatin C, and most preferably, less than about 0.02% by weight pravastatin C.

The present invention provides a method for the purification of pravastatin or pravastatin salts comprising using adsorption chromatography. This method comprises dissolving pravastatin or its salt in water to form an aqueous solution; adjusting the pH of the aqueous solution to a pH of about 6.7 to about 10; adding the aqueous solution to an adsorption column bed, eluting pravastatin with an eluting solution; and collecting fractions having high purity pravastatin. The purification method may be repeated as necessary to achieve the desired pravastatin purity.

The amount of water used should be sufficient to dissolve the pravastatin or pravastatin salt and may be easily determined by one of ordinary skill in the art as the amount may vary depending on the amount of pravastatin or salt. Typically, the amount of water used is about 8 ml of water per gram of pravastatin salt and preferably about 6 ml of water per gram.

The pH of the aqueous solution may be adjusted using any method known in the art. Typically, the pH of the aqueous solution may be adjusted using a basic solution, such as 25% NaOH, in sufficient amount to achieve a pH of about 6.7 to about 10.

Generally, the adsorption column bed includes resins such as polymeric adsorbents with highly porous structures whose internal surfaces can adsorb and then desorb a wide variety of different species depending on the environment in which they are used. In this case, with polar solvents such as water, the polymeric adsorbents exhibit non-polar or hydrophobic behavior and may adsorb organic species that are sparingly soluble. In one embodiment, the adsorption column bed may be a reverse phase silica gel column. Commercially available resins include those manufactured by Rohm and Haas, Philadelphia Pa., such as AMBERLITE™ XAD™ 4, XAD™ 7, XAD™ 16, XAD™ 16HP, XAD™ 761, and XAD™ 1180. Other resins suitable for the process of the invention include those manufactured and sold by Mitsubishi Kasei Corporation, Japan, such as DAION™ HP 10, DAION™ HP 20, DAION™ HP 21, DAION™ HP 30, DAION™ HP 40, DAION™ HP 50, DAION™ SP 800, DAION™ SP 825, DAION™ SP 850, DAION™ SP 875, DAION™ SP 205, DAION™ SP 207, DAION™ HP1MG, and DAION™ HP2MG. Reverse phase silica gels include those manufactured and sold by Merck & Co., Whitehouse Station, N.J., such as C-18, RP-2, RP-8, and RP-18.

Eluting pravastatin or pravastatin salt with an eluting solution is carried out using techniques known to one of ordinary skill in the art. The eluting solution typically comprises water and at least one of acetone, acetonitrile, methanol, ethanol, or isopropanol. Preferably, the ratio of water to acetone, acetonitrile, methanol, ethanol, or isopropanol is about 7:3 to about 9:1 by volume, and more preferably the ratio is 8:2. Thereafter, the fractions with high purity pravastatin are collected, reduced in volume, and dried. See European Pharmacopoeia 4.5 (2003).

The pravastatin produced by this method contains less than about 0.1% by weight pravastatin C. Preferably, pravastatin contains less than about 0.1% by weight pravastatin C, more preferably less than 0.03% by weight, and most preferably, less than about 0.02% by weight.

The present invention further provides purified pravastatin and pravastatin sodium produced by the methods of the invention, and pharmaceutical formulations comprised thereof.

Pharmaceutical formulations of the present invention contain purified pravastatin or compactin, such as disclosed herein. In addition to the active ingredient(s), the pharmaceutical formulations of the present invention may contain one or more excipients. Excipients are added to the formulation for a variety of purposes. Diluents increase the bulk of a solid pharmaceutical composition, and may make a pharmaceutical dosage form containing the composition easier for the patient and care giver to handle. Diluents for solid compositions include, for example, microcrystalline cellulose (e.g. Avicel(®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit®), potassium chloride, powdered cellulose, sodium chloride, sorbitol and talc.

Solid pharmaceutical compositions that are compacted into a dosage form, such as a tablet, may include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate and starch.

The dissolution rate of a compacted solid pharmaceutical composition in the patient's stomach may be increased by the addition of a disintegrant to the composition. Disintegrants include alginic acid, carboxymethylcellulose calcium, carboxymethylcellulose sodium (e.g. Ac-Di-Sol®, Primellose®), colloidal silicon dioxide, croscarmellose sodium, crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab®) and starch.

Glidants can be added to improve the flowability of a non-compacted solid composition and to improve the accuracy of dosing. Excipients that may function as glidants include, but are not limited to, colloidal silicon dioxide, magnesium trisilicate, powdered cellulose, starch, talc and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc and zinc stearate.

Flavoring agents and flavor enhancers make the dosage form more palatable to the patient. Common flavoring agents and flavor enhancers for pharmaceutical products that may be included in the composition of the present invention include, but are not limited to, maltol, vanillin, ethyl vanillin, menthol, citric acid, fumaric acid, ethyl maltol and tartaric acid.

Solid and liquid compositions may also be dyed using any pharmaceutically acceptable colorant to improve their appearance and/or facilitate patient identification of the product and unit dosage level.

In liquid pharmaceutical compositions of the present invention, pravastatin of compactin, in combination with any other solid excipients are dissolved or suspended in a liquid carrier such as water, vegetable oil, alcohol, polyethylene glycol, propylene glycol or glycerin.

Liquid pharmaceutical compositions may contain emulsifying agents to disperse uniformly throughout the composition an active ingredient or other excipient that is not soluble in the liquid carrier. Emulsifying agents that may be useful in liquid compositions of the present invention include, for example, gelatin, egg yolk, casein, cholesterol, acacia, tragacanth, chondrus, pectin, methyl cellulose, carbomer, cetostearyl alcohol and cetyl alcohol.

Liquid pharmaceutical compositions of the present invention may also contain a viscosity enhancing agent to improve the mouth-feel of the product and/or coat the lining of the gastrointestinal tract. Such agents include, but are not limited to, acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth and xanthan gum.

Sweetening agents such as sorbitol, saccharin, sodium saccharin, sucrose, aspartame, fructose, mannitol and invert sugar may be added to improve the taste.

Preservatives and chelating agents such as alcohol, sodium benzoate, butylated hydroxyl toluene, butylated hydroxyanisole and ethylenediamine tetraacetic acid may be added at levels safe for ingestion to improve storage stability.

According to the present invention, a liquid composition may also contain a buffer such as guconic acid, lactic acid, citric acid or acetic acid, sodium guconate, sodium lactate, sodium citrate or sodium acetate. Selection of excipients and the amounts used may be readily determined by the formulation scientist based upon experience and consideration of standard procedures and reference works in the field.

The solid compositions of the present invention include powders, granulates, aggregates and compacted compositions. The dosages include dosages suitable for oral, buccal, rectal, parenteral (including subcutaneous, intramuscular, and intravenous), inhalant and ophthalmic administration. Although the most suitable administration in any given case will depend on the nature and severity of the condition being treated, the most preferred route of the present invention is oral. The dosages may be conveniently presented in unit dosage form and prepared by any of the methods well-known in the pharmaceutical arts.

Dosage forms include solid dosage forms like tablets, powders, capsules, suppositories, sachets, troches and losenges, as well as liquid syrups, suspensions and elixirs.

The dosage form of the present invention may be a capsule containing the composition, preferably a powdered or granulated solid composition of the invention, within either a hard or soft shell. The shell may be made from gelatin and optionally contain a plasticizer such as glycerin and sorbitol, and an opacifying agent or colorant.

The active ingredient and excipients may be formulated into compositions and dosage forms according to methods known in the art.

A composition for tableting or capsule filling may be prepared by wet granulation. In wet granulation, some or all of the active ingredients and excipients in powder form are blended and then further mixed in the presence of a liquid, typically water, that causes the powders to clump into granules. The granulate is screened and/or milled, dried and then screened and/or milled to the desired particle size. The granulate may then be tableted, or other excipients may be added prior to tableting, such as a glidant and/or a lubricant.

A tableting composition may be prepared conventionally by dry blending. For example, the blended composition of the actives and excipients may be compacted into a slug or a sheet and then comminuted into compacted granules. The compacted granules may subsequently be compressed into a tablet.

As an alternative to dry granulation, a blended composition may be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate and colloidal silica. The proper use of these and other excipients in direct compression tableting is known to those in the art with experience and skill in particular formulation challenges of direct compression tableting.

A capsule filling of the present invention may comprise any of the aforementioned blends and granulates that were described with reference to tableting, however, they are not subjected to a final tableting step.

The dosage of PLAVIX may be used as guidance. PLAVIX is administered orally. The recommended oral dose of PLAVIX is 75 mg once daily.

Having described the invention with reference to certain preferred embodiments, other embodiments will become apparent to one skilled in the art from consideration of the specification. The invention is further defined by reference to the following examples describing in detail the preparation of the composition and methods of use of the invention. It will be apparent to those skilled in the art that many modifications, both to materials and methods, may be practiced without departing from the scope of the invention.

EXAMPLES

The fermentation and recovery of pravastatin was carried out using methods commonly known to one skilled in the art, such as those described in U.S. Pat. No. 6,444,452, hereby incorporated by reference.

Example 1

Pravastatin Synthesis

Analysis of the starting compactin by HPLC using a Waters column RP-18 (5 m, 2.1×150 mm) with a mobile phase of (a) 0.1% phosphoric acid and the pH adjusted with 25% NaOH and (b) a mixture of distilled water and acetonitrile (1:9). The column was run for 50 min at 40° C. using a detection wavelength of 240 nm. The amount of compactin was determined using a standardized solution of 10 mg of compactin and 10 mg compactin ammonium salt.

TABLE 1

HPLC compactin analysis

| Time (min) | % of solution (a) | % of solution (b) |
|---|---|---|
| 0 | 70 | 30 |
| 7 | 70 | 30 |
| 18 | 55 | 45 |
| 33 | 30 | 70 |
| 42 | 10 | 90 |
| 42.1 | 70 | 30 |
| 50 | 70 | 30 |

The samples were prepared in 0.4 mg/ml concentrations and the impurity profile was determined as the peak area compared to the standardized sample. For this sample, the impurity compactin C in an amount of 0.25% by weight.

The pure compactin was then fermented into pravastatin and isolated according to the methods disclosed in U.S. Pat. No. 6,444,452. Analysis of the pravastatin salt by HPLC determined that the impurity pravastatin C was present in an amount of 0.12% by weight.

Example 2

Pravastatin Purification

The pravastatin salt from Example 1 (90 g) was dissolved in water (540 ml), thereafter, the pH was adjusted to 6.7 to 10 using 25% NaOH. The pravastatin salt solution was passed through a sorption resin bed (550 ml of sorption resin XAD™ 1180). The column diameter was 3.2 cm and the applied flow rate was 90 ml/hour. After adsorption of pravastatin salt, the column was eluted with 4 L of water:acetone (8:2) and the fractions containing pravastatin were combined (1760 ml), reduced in volume, and pravastatin salt (64.8 g) was isolated. Impurity analysis by HPLC, as described in European Pharmacopoeia, determined that pravastatin C was present in an amount of 0.04% by weight.

Example 3

Purification of Compactin

A compactin sample with compactin C present in an amount of 0.2% by weight was purified by crystallization. The compactin sample (30 g) was suspended in acetone (5 times by volume) and heated to reflux. Water (1.25 times by volume) was added to the heated suspension, and the solution was allowed to cool to 20° C. at a cooling rate of 2° C./hour. Upon cooling, crystals formed which were stirred for 2 hours at 20° C., and subsequently collected by filtration, washed with a water:acetone (1:1) solution, and dried. After drying, the crystalline compactin (28.2 g) was collected and analyzed by HPLC, as described in the European Pharmacopoeia. The crystalline compactin had 0.15% by weight of compactin C.

Example 4

Synthesis of High Purity Pravastatin

A compactin sample with compactin C in an amount of 0.2% by weight was purified by crystallization. The compactin sample (30 g) was suspended in methanol (5 times by volume) and heated to reflux. Water (1.5 times by volume) was added to the heated suspension, and the solution was allowed to cool to 20° C. at a cooling rate of 2° C./hour. Thereafter, the solution was heated to 30° C. and stirred for 16 hours. Upon cooling, crystals formed which were collected by filtration, washed with a water: methanol (1:1) solution, and dried. After drying, the crystalline compactin (27.2 g) was collected and analyzed by HPLC. The crystalline compactin had 0.15% by weight of compactin C.

The pure compactin is then fermented into pravastatin and pravastatin is isolated according to the methods disclosed in U.S. Pat. No. 6,444,452. Achievable pravastatin C level is 0.02% by weight.

Example 5

Synthesis of High Purity Pravastatin

A compactin sample with compactin C in an amount of 0.2% by weight was purified by crystallization. The compactin sample (30 g) was suspended in isopropanol (5 times by volume) and heated to reflux. Water (1.5 times by volume) was added to the heated suspension, and the solution was allowed to cool to 25° C. at a cooling rate of 2° C./hour. Upon cooling, crystals formed which were collected by filtration, washed with a water:isopropanol (1:1) solution, and dried. After drying, the crystalline compactin (22.9 g) was collected and analyzed by HPLC. The crystalline compactin had 0.16% by weight of compactin C.

The pure compactin is then fermented into pravastatin and isolated according to the methods disclosed in U.S. Pat. No. 6,444,452. Achievable pravastatin C level is 0.03% by weight.

Example 6

Synthesis of High Purity Pravastatin

A compactin sample with compactin C in an amount of 0.2% by weight was purified by crystallization. The compactin sample (30 g) was suspended in acetonitrile (5 times by volume) and heated to reflux. Water (1.5 times by volume) was added to the heated suspension, and the solution was allowed to cool to 25° C. at a cooling rate of 2° C./hour. Upon cooling, crystals formed which were collected by filtration, washed with a water:acetonitrile (1:1) solution, and dried. After drying, the crystalline compactin (24.2 g) was collected and analyzed by HPLC. The crystalline compactin had 0.15% by weight of compactin C.

The pure compactin is then fermented into pravastatin and isolated according to the methods disclosed in U.S. Pat. No. 6,444,452. Achievable pravastatin C level is 0.02% by weight.

What is claimed is:

1. A method of synthesizing a pravastatin composition containing less than about 0.1% pravastatin C by weight, said process comprising:
    a) obtaining at least one sample of at least one batch containing compactin and compactin C;
    b) measuring the level of compactin C in each of the samples of a);
    c) selecting a compactin batch that contains compactin C, wherein the amount of compactin C in the selected batch is about 0.16% or less by weight; and
    d) hydroxylating the batch selected in c) to synthesize said pravastatin.

2. The method of claim 1, wherein the selected compactin batch of step c) contains about 0.15% or less of compactin C by weight.

3. A method of synthesizing a pravastatin composition containing less than about 0.1% pravastatin C by weight, said process comprising:
    a) purifying a compactin composition containing compactin C to obtain a composition containing compactin C in an amount that is about 0.16% or less by weight, and
    b) hydroxylating the composition resulting from a) to synthesize pravastatin.

4. The method of claim 3, wherein the purification in step a) comprises:
    a) dissolving or suspending a compactin composition containing compactin C in at least one water miscible organic solvent;
    b) adding water to the solution or suspension formed in a) at a ratio of about 0.16 to about 0.4 based on the volume of the water miscible organic solvent to obtain a mixture;
    c) cooling the mixture formed in b); and
    d) recovering the compactin composition containing compactin C in an amount that is about 0.16% or less by weight.

5. The method of any one of claims 3 and 4, wherein the purified compactin composition contains about 0.15% or less compactin C by weight.

6. A method of synthesizing a pravastatin composition containing less than about 0.1% pravastatin C by weight comprising:
    a) dissolving or suspending a compactin composition containing compactin C in at least one water miscible organic solvent;
    b) adding water to the solution or suspension formed in a) at a ratio of about 0.16 to about 0.4 based on the volume of the water miscible organic solvent to obtain a mixture;
    c) cooling the mixture formed in b);
    d) isolating a sample of the compactin composition containing compactin C recovered from the cooled mixture;
    e) measuring the quantity of compactin C in the isolated sample from d);
    f) determining if the quantity of compactin C in e) is about 0.16% or less by weight; and if the quantity of compactin C measured in e) is greater than about 0.16% by weight, then:

g) purifying by crystallization the composition resulting from d) until the quantity of compactin C is about 0.16% or less by weight, and hydroxylating the purified composition to synthesize the pravastatin; or, if the quantity of compactin C measured in e) is about 0.16% or less by weight, then:

h) hydroxylating the composition of step d) to synthesize the pravastatin.

7. The method of any one of claims 1, 3 and 6, wherein the pravastatin is synthesized by fermentation of compactin.

8. The method of any one of claims 4 and 6, wherein the water miscible solvent is selected from the group consisting of $C_{3-5}$ ketones, nitriles, and $C_{1-4}$ alcohols.

9. The method of any one of claims 4 and 6, wherein the water miscible organic solvent is at least one of acetone, methanol, ethanol, n-propanol, isopropanol, acetonitrile, methyl-ethyl-ketone, or tetrahydrofuran.

10. The method of any one of claims 4 and 6, wherein the water in step b) is added at a ratio of about 0.17 to about 0.4 based on the volume of the water miscible organic solvent.

11. The method of any one of claims 4 and 6, wherein step a) is performed at a temperature of about 30° C. to about the reflux temperature of the water miscible organic solvent.

12. The method of any one of claims 4 and 6, wherein the amount of the water miscible organic solvent in step a) is about 5 times the mass of compactin.

13. The method of any one of claims 4 and 6, wherein the cooling in step c) is to a temperature of about 0° C. to about 30° C.

14. The method of claim 13, wherein the cooling in step c) is to a temperature of about 15° C. to about 30° C.

15. The method of claim 14, wherein the cooling in step c) is to a temperature of about 20° C. to about 25° C.

16. The method of any one of claims 4 and 6, wherein the cooling in step c) is performed at a rate of about 1° C. per hour to about 6° C. per hour.

17. The method of claim 16, wherein the cooling in step c) is performed at a rate of about 2° C. per hour to about 4° C. per hour.

18. The method of any one of claims 4 and 6, further comprising, prior to step d), heating to a temperature of about 30° C. for 16 hours, followed by cooling for a second time.

19. The method of any one of claims 4 and 6, further comprising drying the composition obtained in d).

20. A method of separating pravastatin from pravastatin C, said method comprising:
a) dissolving pravastatin or a salt thereof in water to form an aqueous solution;
b) adjusting the pH of the aqueous solution to a pH in the range from about 6.7 to about 10;
c) adding the aqueous solution to an adsorption column bed;
d) eluting pravastatin with an eluting solution; and
e) collecting fractions having pure pravastatin;
wherein the separation of pravastatin from pravastatin C is carried out by adsorption chromatography.

21. The method of claim 20, wherein the purified pravastatin composition contains pravastatin C in an amount that is less than about 0.1% by weight.

22. The method of claim 20, wherein the amount of water used to dissolve the pravastatin or a salt thereof is between about 6 ml of water per gram of the pravastatin or pravastatin salt and 8 ml of water per gram of the pravastatin or pravastatin salt.

23. The method of claim 22, wherein the amount of water used to dissolve the pravastatin or salt thereof is about 6 ml of water per gram of the pravastatin or pravastatin salt.

24. The method of claim 20, wherein the pH of the aqueous solution is adjusted using a basic solution in sufficient amount to achieve a pH of about 6.7 to about 10.

25. The method of claim 20, wherein the basic solution used to adjust the pH is NaOH.

26. The method of claim 20, wherein the adsorption column bed includes resins or a reverse phase silica gel.

27. The method of claim 20, wherein the eluting solution comprises water and at least one of acetone, acetonitrile, methanol, ethanol, or isopropanol.

28. The method of claim 27, wherein the ratio of water to acetone, acetonitrile, methanol, ethanol, or isopropanol is about 7:3 to about 9:1 by volume.

29. The method of claim 28, wherein the ratio of water to acetone, acetonitrile, methanol, ethanol, or isopropanol is about 8:2 by volume.

30. The method claim 1, wherein the synthesized pravastatin composition contains pravastatin C in an amount that is about 0.04% or less by weight.

31. The method of claim 30, wherein the pravastatin composition contains pravastatin C in an amount that is about 0.03% or less by weight.

32. The method of claim 30, wherein the pravastatin composition contains pravastatin C in an amount that is about 0.02% or less by weight.

33. The method claim 3, wherein the synthesized pravastatin composition contains pravastatin C in an amount that is about 0.04% or less by weight.

34. The method of claim 33, wherein the pravastatin composition contains pravastatin C in an amount that is about 0.03% or less by weight.

35. The method of claim 33, wherein the pravastatin composition contains pravastatin C in an amount that is about 0.02% or less by weight.

36. The method claim 6, wherein the synthesized pravastatin composition contains pravastatin C in an amount that is about 0.04% or less by weight.

37. The method of claim 36, wherein the pravastatin composition contains pravastatin C in an amount that is about 0.03% or less by weight.

38. The method of claim 36, wherein the pravastatin composition contains pravastatin C in an amount that is about 0.02% or less by weight.

39. The method of claim 21, wherein the purified pravastatin composition contains pravastatin C in an amount that is about 0.03% or less by weight.

40. The method of claim 39, wherein the pravastatin composition contains pravastatin C in an amount that is about 0.02% or less by weight.

41. The method of claim 8, wherein the water miscible solvent is selected from the group consisting of $C_{3-5}$ ketones, acetonitrile, and $C_{1-4}$ alcohols.

42. The process of claim 20, wherein the pravastatin salt is pravastatin sodium.

* * * * *